US00PP31541P2

(12) United States Plant Patent
Klemm et al.

(10) Patent No.: US PP31,541 P2
(45) Date of Patent: Mar. 10, 2020

(54) ***OSTEOSPERMUM* PLANT NAMED 'KLEOE18301'**

(50) Latin Name: ***Osteospermum ecklonis* Norl.**
Varietal Denomination: KLEOE18301

(71) Applicant: Klemm+Sohn GmbH & Co. KG, Stuttgart (DE)

(72) Inventors: Nils Klemm, Stuttgart (DE); Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,842

(22) Filed: Jun. 17, 2019

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./360
CPC ..... A01H 5/02; A01H 6/14
See application file for complete search history.

*Primary Examiner* — Annette H Para
(74) *Attorney, Agent, or Firm* — Barbara Campbell; Cochran Freund & Young LLC

(57) ABSTRACT

A new *Osteospermum* plant particularly distinguished by white flowers with blue discs and an upright growth habit, is disclosed.

1 Drawing Sheet

Genus and species: *Osteospermum ecklonis* Norl.
Variety denomination: 'KLEOE18301'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE18301'. 'KLEOE18301' originated from a cross-pollination conducted in August to September 2011 in Stuttgart, Germany between the proprietary female *Osteospermum* variety 'OE-2010-0382' (unpatented), and the male *Osteospermum* variety 'Sunny', also known as 'OE-2000-Pingo' (patent status unknown).

The seeds from the cross were sown and plants were grown in a greenhouse for evaluation, where an individual plant designated 'KLEOE18301' was selected from the group of plants in May 2011 in Stuttgart. In June 2011 in Stuttgart, 'KLEOE18301' was first vegetatively propagated by vegetative terminal cuttings. 'KLEOE18301' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. White ray florets with blue discs; and
2. An upright growth habit.

DESCRIPTION OF THE PHOTOGRAPH

This new *Osteospermum* plant is illustrated by the accompanying photograph which shows the plant's overall plant habit including form, foliage, and flowers. The photograph is of a 12-week-old plant grown in a greenhouse in Stuttgart, Germany in May 2019.

The colors shown are as true as can be reasonably obtained by conventional photographic procedures.

DESCRIPTION OF THE NEW VARIETY

The following detailed descriptions set forth the distinctive characteristics of 'KLEOE18301'. The data which define these characteristics were collected in Latina, Italy on May 16, 2019 on plants that had been potted in week 45 of 2018. Color references are to The R.H.S. Colour Chart of The Royal Horticultural Society of London (R.H.S.), 5$^{th}$ edition (2007).

Classification:
- *Family*.—Asteraceae.
- *Botanical*.—*Osteospermum ecklonis*.
- *Common*.—*Osteospermum*.
- *Designation*.—'KLEOE18301'.

Parentage:
- *Female parent*.—The proprietary female *Osteospermum* variety 'OE-2010-0382' (unpatented).
- *Male parent*.—The male *Osteospermum* variety 'Sunny' (patent status unknown).

Plant:
- *Form and habit*.—Herbaceous perennial but usually cultivated as an annual; not frost resistant.
- *Growth habit*.—Upright.
- *Branching habit*.—Normal.
- *Height* (*from top of soil, including inflorescence*).—29.4 cm.
- *Width* (*including inflorescences*).—27.5 cm.
- *Propagation type*.—Stem cuttings; vegetative terminal tip cuttings.
- *Time to produce a finished flowering plant*.—9 weeks.
- *Time to initiate and develop roots*.—4 weeks.
- *Root description*.—Fine and white, RHS 155A.

Stems:
- *Total number of branches per plant* (*calculated at the base of the plant*).—6.

*Length.*—27.0 cm.
*Diameter.*—0.9 cm.
*Internode length.*—3.9 cm.
*Color.*—RHS 143B.
*Texture.*—Smooth.
*Anthocyanin.*—Absent.

Leaves:
*Arrangement.*—Alternate.
*Shape.*—Obovate.
*Apex.*—Obtuse.
*Base.*—Acute.
*Margin.*—Entire.
*Immature color.*—Upper surface: RHS 143A. Lower surface: RHS 143B.
*Mature color.*—Upper surface: RHS N137A. Lower surface: RHS 138A. Length: 7.1 cm. Width: 4.1 cm.
*Texture.*—Upper surface: Leathery. Lower surface: Leathery with fine hairs.
*Petioles.*—Absent.
*Venation pattern.*—Pinnate.
*Venation color.*—Upper surface: RHS N137A. Lower surface: RHS 138A.

Flower buds:
*Shape.*—Round-ovoid.
*Length.*—1.1 cm.
*Diameter.*—0.9 cm.
*Color* (*at tight bud just before the ray florets unfold*).—RHS 138A.

Inflorescence:
*Type.*—Composite, single.
*Blooming habit.*—Upright, with flower stems.
*Quantity of inflorescences per plant.*—23.
*Lastingness of the inflorescences on the plant.*—10 to 15 days.
*Fragrance.*—Present.
*Inflorescence diameter.*—6.5 cm.
*Inflorescence depth.*—0.9 cm.
*Disc diameter.*—1.2 cm.

Disc floret:
*Quantity per inflorescence.*—36.
*Shape.*—Tubular.
*Tube color.*—Closed: RHS NN155A. Mature: RHS N115B.
*Length.*—0.6 cm.
*Diameter* (*at apex*).—0.2 cm.
*Apex.*—Acute.
*Apex color.*—RHS 79A.
*Base.*—Acute.
*Base color.*—RHS 145D.
*Margin.*—Entire.

Ray floret:
*Quantity per inflorescence.*—16.
*Shape.*—Oblanceolate.
*Color.*—Upper surface: RHS NN155C (apical), RHS NN155C (Middle), and RHS N82B (basal). Lower surface: Main color RHS N155A with stripes colored RHS 97A.
*Length.*—3.6 cm.
*Width.*—1.1 cm.
*Apex.*—Obtuse.
*Base.*—Acute.
*Margin.*—Entire.
*Texture* (*both surfaces*).—Smooth.

Peduncle:
*Length.*—10.1 cm.
*Diameter.*—0.2 cm.
*Texture.*—Smooth with hairs.
*Color.*—RHS 143C.

Phyllaries:
*Arrangement.*—Single.
*Observed quantity per flower.*—15.
*Shape.*—Lanceolate.
*Apex.*—Acute.
*Base.*—Obtuse.
*Margin.*—Entire.
*Length.*—0.9 cm.
*Width.*—0.2 cm.
*Texture.*—Upper surface: Smooth with fine hairs. Lower surface: Smooth.
*Color.*—Upper surface: RHS 143A. Lower surface: RHS 138A.

Reproductive organs:
*Androecium.*—Location: On disc and ray florets. Stamens: Shape: Filamentous. Quantity: Numerous, 70 to 100. Filament length: 0.5 cm. Filament diameter: less than 0.1 cm. Anther: Shape: Lanceolate. Color: RHS 77A. Length: 0.3 cm. Diameter: Less than 0.1 cm. Pollen: Color: RHS 17A. Amount: Sparse.
*Gynoecium.*—Location: On the phyllary. Pistils: Number: Numerous, 50 to 70. Length: 0.6 cm. Diameter: Less than 0.1 cm. Stigma: Color: RHS 79A. Shape: Tapering filamentous and split in two parts. Length: Less than 0.1 cm. Diameter: Less than 0.1 cm. Style: Color: RHS NN155A. Length: 0.3 cm. Diameter: Less than 0.1 cm.

Fruit and seed set: None observed to date.

Disease and pest/insect resistance: No disease and pest/insect resistance observed.

COMPARISON WITH PARENTAL LINES AND KNOWN VARIETY

'KLEOE18301' is a distinct variety of *Osteospermum* and is distinguished from its parents as described in Table 1.

TABLE 1

| Characteristic | 'KLEOE18301' | Female Parent 'OE-2010-0382' | Male Parent 'Sunny' |
|---|---|---|---|
| Disc Color | Blue | Blue | Yellow |
| Earliness | Medium late | Late | Early |

'KLEOE18301' is most similar to the commercial *Osteospermum* variety 'Flower Power Light Pink'. Differences between the varieties are described in Table 2.

TABLE 2

| Comparison with Similar Variety | | |
|---|---|---|
| Characteristic | 'KLEOE18301' | 'Flower Power Light Pink' |
| Flower color | White | Light Pink |
| Growth | Medium | Compact |
| Earliness | Medium early | Early |

We claim:

1. A new and distinct variety of *Osteospermum* plant designated 'KLEOE18301' as illustrated and described herein.

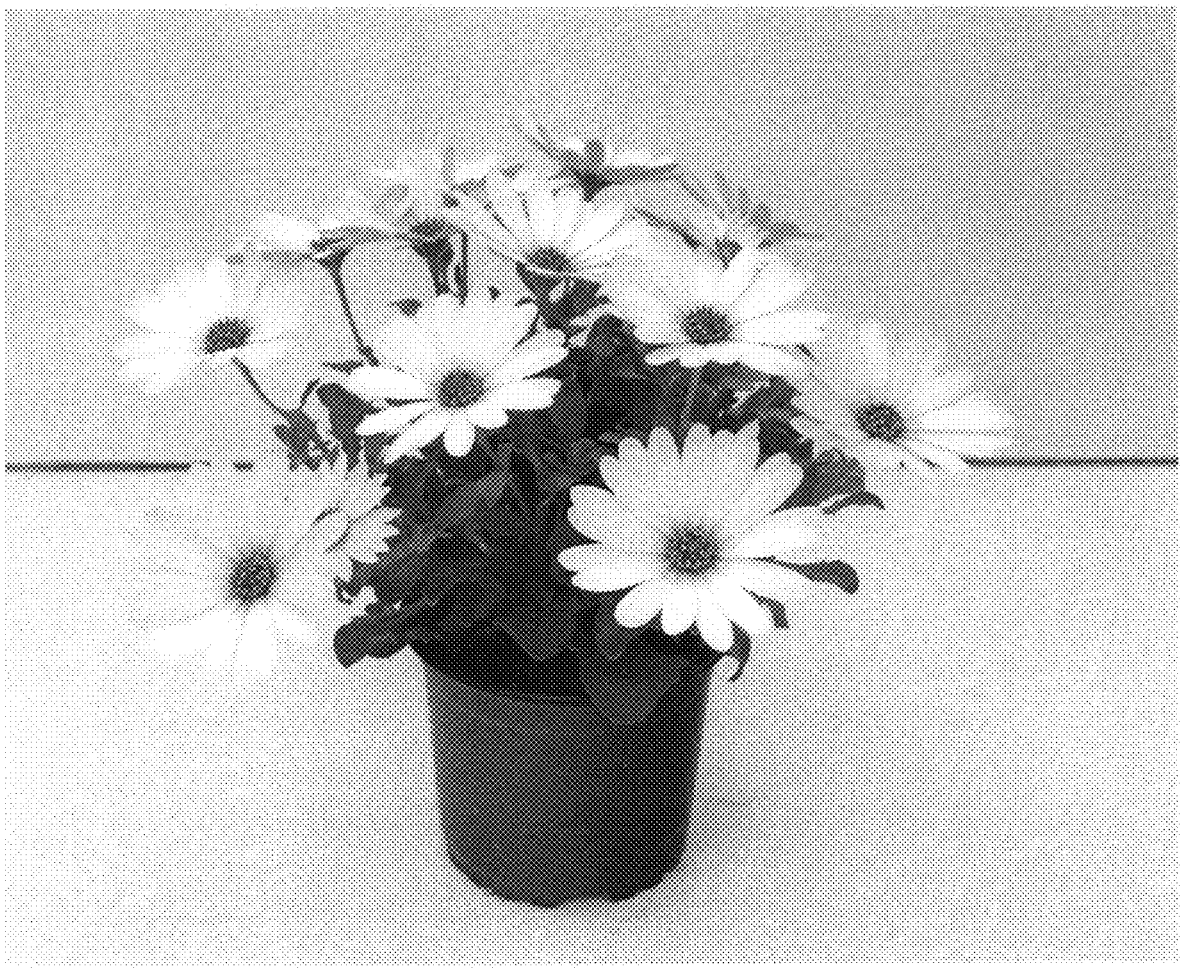

* * * * *